(12) United States Patent
Lick et al.

(10) Patent No.: US 10,426,593 B2
(45) Date of Patent: Oct. 1, 2019

(54) EXPANSIBLE CARDIOVASCULAR GRAFT SYSTEM

(71) Applicants: Arizona Board of Regents on Behalf of The University of Arizona, Tucson, AZ (US); Banner Health, Phoenix, AZ (US)

(72) Inventors: Scott D. Lick, Tucson, AZ (US); Richard G. Smith, Tucson, AZ (US)

(73) Assignees: Arizona Board of Regents on Behalf of The University of Arizona, Tucson, AZ (US); Banner Health, Phoenix, AZ (US)

( * ) Notice: Subject to any disclaimer, the term of this patent is extended or adjusted under 35 U.S.C. 154(b) by 0 days.

(21) Appl. No.: 15/557,012

(22) PCT Filed: Mar. 11, 2016

(86) PCT No.: PCT/US2016/022152
§ 371 (c)(1),
(2) Date: Sep. 8, 2017

(87) PCT Pub. No.: WO2016/145391
PCT Pub. Date: Sep. 15, 2016

(65) Prior Publication Data
US 2018/0071075 A1 Mar. 15, 2018

Related U.S. Application Data

(60) Provisional application No. 62/131,665, filed on Mar. 11, 2015.

(51) Int. Cl.
*A61F 2/06* (2013.01)
(52) U.S. Cl.
CPC .......... *A61F 2/06* (2013.01); *A61F 2002/061* (2013.01); *A61F 2210/0057* (2013.01);
(Continued)

(58) Field of Classification Search
CPC ........ A61F 2/06; A61F 2/07; A61F 2002/823; A61F 2002/075
See application file for complete search history.

(56) References Cited

U.S. PATENT DOCUMENTS 4,938,766 A * 7/1990 Jarvik ..................... A61F 2/06
623/3.17
6,352,554 B2 3/2002 De Paulis
(Continued)

FOREIGN PATENT DOCUMENTS

WO WO2004021925 A1 3/2004
WO WO2006036373 A2 4/2006
(Continued)

OTHER PUBLICATIONS

Asmar et al., Aortic Distensibility in Normotensive, Untreated and Treated Hypertensive Patients. 1995, Blood Pressure 4:48-54. Abstract.
(Continued)

*Primary Examiner* — Brian A Dukert
(74) *Attorney, Agent, or Firm* — Nguyen Tarbet

(57) ABSTRACT

An expansible cardiovascular graft system for replacing vasculature such as a portion of the aorta. The portion of the aorta may include but is not limited to the ascending aorta, the aortic arch, or the descending aorta. The system features a graft conduit with a proximal anchor disposed at the proximal end and a distal anchor disposed at the distal end and an expansible portion disposed between the proximal anchor and the distal anchor. At least a portion of the expansible system is adapted to gradually expand.

20 Claims, 9 Drawing Sheets

Systole   Diastole

(52) U.S. Cl.
CPC .............. *A61F 2210/0076* (2013.01); *A61F 2220/0008* (2013.01); *A61F 2250/0018* (2013.01)

(56) References Cited

U.S. PATENT DOCUMENTS

| | | | |
|---|---|---|---|
| 7,318,838 | B2 | 1/2008 | Henderson |
| 7,655,035 | B2 | 2/2010 | Sowinski et al. |
| 7,658,706 | B2 | 2/2010 | Squillace |
| 7,717,952 | B2 | 5/2010 | Case et al. |
| 7,722,665 | B2 | 5/2010 | Anwar et al. |
| 7,758,633 | B2 | 7/2010 | Nazzaro |
| 7,785,438 | B2 | 8/2010 | Jensen |
| 7,806,922 | B2 | 10/2010 | Henderson et al. |
| 7,833,263 | B2 | 11/2010 | Thistle |
| 7,857,843 | B2 | 12/2010 | Henderson |
| 7,901,446 | B2 | 3/2011 | Fitzpatrick et al. |
| 8,038,690 | B2 | 10/2011 | Borghi |
| 8,066,758 | B2 | 11/2011 | Bogert et al. |
| 8,123,797 | B2 | 2/2012 | Anwar et al. |
| 8,163,002 | B2 | 4/2012 | Weinberg |
| 8,221,492 | B2 | 7/2012 | Case et al. |
| 8,353,814 | B2 | 1/2013 | Villafana et al. |
| 8,388,679 | B2 | 3/2013 | Du |
| 8,475,477 | B2 | 7/2013 | Borgi |
| 8,728,152 | B2 | 5/2014 | Goldmann et al. |
| 2003/0055491 | A1 | 3/2003 | Schwartz et al. |
| 2008/0132993 | A1 | 6/2008 | Rasmussen et al. |
| 2009/0093873 | A1 | 4/2009 | Navia |
| 2013/0226286 | A1* | 8/2013 | Hargreaves ............... A61F 2/06 623/1.26 |
| 2014/0324154 | A1* | 10/2014 | Shalev ...................... A61F 2/07 623/1.13 |

FOREIGN PATENT DOCUMENTS

| | | |
|---|---|---|
| WO | WO2008007397 A1 | 1/2008 |
| WO | WO2008016578 A3 | 2/2008 |
| WO | WO2013030818 A2 | 3/2013 |
| WO | WO2014163957 A1 | 10/2014 |

OTHER PUBLICATIONS

Benetos et al., Influence of Age, Risk Factors, and Cardiovascular and Renal Disease on Arterial Stiffness: Clinical Applications 2002, Am Journ Hyperten 15:1101-1108.

Bentall & Debono. A technique for complete replacement of the ascending aorta. Thorax. Jul. 1968;23(4):338-9.

De Paulis, R et al. A Third Generation of Ascending Aorta Dacron Graft: Preliminary Experience . Ann Thorac Surg. 2008, 309, 85:305-9.

Kelly et al., Noninvasive Determination of Age-Related Changes in the Human Arterial Pulse, 1989, Circulation 80:1652-1659.

Kirsch ME et al. Bioprosthetic replacement of the ascending thoracic aorta: what are the options? Eur J Cardiothorac Surg. Jan. 2009;35(1):77-82.

Kouchoukos NT et al. Replacement of the Ascending Aorta and Aortic Valve with a Composite Graft: Results in 86 Patients. Ann Surg. Sep. 1980; 192(3): 403-412.

Merillon, J.P. et al. Left ventricular performance is closely related to the physical properties of the arterial system: Landmark clinical investigations in the 1970s and 1980s. Arch Cardiovasc Dis. 2014;107:554-562.

Nishibe T et al. Optimal prosthetic graft design for small diameter vascular grafts. Vascular. Nov.-Dec. 2007;15(6):356-60. Abstract.

Scuteri, A., Tesauro, M., Guglini, L. et al, Aortic stiffness and hypotension episodes are associated with impaired cognitive function in older subjects with subjective complaints of memory loss. Int. J Intern Journ Cardiol 169:371-377; 2013 Abstract.

Vara DS et al, Pathol Biol (Paris). Cardiovascular tissue engineering: state of the art. Dec. 2005;53(10):599-612.

* cited by examiner

Systole          Diastole

EXPANSIBLE CARDIOVASCULAR GRAFT SYSTEM

CROSS REFERENCE

This application claims priority to U.S. Provisional Patent Application No. 62/131,665 filed Mar. 11, 2015, the specification(s) of which is/are incorporated herein in their entirety by reference.

FIELD OF THE INVENTION

The present invention relates to cardiovascular grafts, more particularly to aortic grafts.

BACKGROUND OF THE INVENTION

Aneurysmal segments of the aorta are usually replaced because they are prone to rupture. Also, patients who suffer from senile aortic valve stenosis often require aortic valve replacement (AVR), and in many of those patients, concomitant aneurysmal disease requires the replacement of all or a portion of the ascending aorta.

With age, the aorta tends to dilate and stiffen. A stiffened aorta conducts a pressure wave (incident wave) faster, leading to a faster return pressure wave (reflected wave). This faster reflected wave may have deleterious effects: it can widen pulse pressure (the difference between systolic and diastolic pressure) and can give a higher systolic pressure due to summation with the incident wave. Indeed, wave reflections were observed to be responsible for an increase of about 25% in pulse pressure between the ages of 30 and 60 years (Kelley et al., 1989, Circulation 80:1652-1659). The consequences of the higher systolic pressures and widened pulse pressures due to aorta stiffening may include increases in heart strain and cognitive dysfunction (Scuteri, 2013, Intern Journ Cardiol 169:371-377; Merillon, 2014, Arch Cardiovas Disease 107:554-562). Yet, stiffness and non-compliance of the aorta is not a typical indication for replacement.

The present invention features an expansible cardiovascular graft system for replacing a portion of a vessel, e.g., the aorta, e.g., all or a portion of the ascending aorta. The expansible cardiovascular graft system allows for gradual expansion (e.g., in systole) and recoil (e.g., in diastole). The expansible cardiovascular graft system is not limited to use in the aorta.

The present invention also features methods of treating cardiovascular conditions such as aneurysmal disease by replacing a portion of the aorta (or other appropriate vessel) with the cardiovascular graft system of the present invention. The present invention is not limited to treating aneurysmal vessels. For example, in some embodiments, the graft system of the present invention is used to replace a portion of (or all of) a stiffened vessel, e.g., a stiffened portion of the aorta. This may or may not be subsequent to AVR.

Non-limiting examples of replaceable cardiovascular segments include the infrarenal aorta, the descending thoracic aorta, and the ascending thoracic aorta. The system of the present invention is not limited to vessel replacement; for example, in some embodiments, the system of the present invention is incorporated into a catheter system. In some embodiments, the system of the present invention is used as an endovascular graft. In this example, remaining vascular tissue (e.g., aneurysmal tissue) may create a protected space around the graft, which may delay potential encasement in scar tissue.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DESCRIPTION OF PREFERRED EMBODIMENTS

Figure 1:
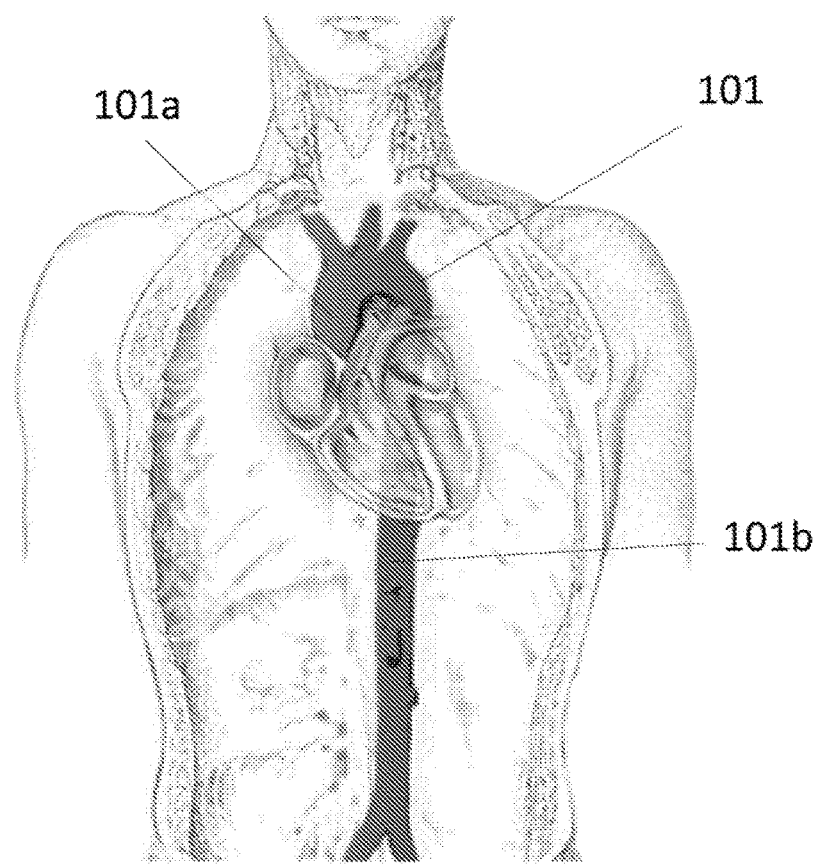
FIG. 1 shows a schematic view of the heart and the aorta (aortic valve/sinuses of valsava not shown).

Following is a list of elements corresponding to a particular element referred to herein:
  50 model heart
  55 model aorta graft
  100 expansible cardiovascular graft system
  101 aorta
  101*a* ascending aorta
  101*b* descending aorta
  110 graft conduit
  111 proximal end of graft conduit
  112 distal end of graft conduit
  113 midsection of graft conduit 121 proximal anchor
121a inner edge of proximal anchor
122 distal anchor
122a inner edge of distal anchor
125 serration
130 expansible portion
130a first expansible portion segment
130b second expansible portion segment
130c third expansible portion segment
130d fourth expansible portion segment
130e fifth expansible portion segment
131 first distance
140 catheter
150 secondary channel
150a expansible portion of secondary channel Graft System Referring now to FIG. 1-9, the present invention features an expansible cardiovascular graft system (100) for replacing a portion of a vessel such as the aorta (101), e.g., all or a portion of the ascending aorta (101a) (for reference, FIG. 1 shows ascending aorta (101a) and descending aorta (101b)). The expansible cardiovascular graft system (100) is not limited to use in the aorta. The system (100) of the present invention is not limited to use as only a vessel replacement graft. For example, in some embodiments, the system (100) of the present invention is incorporated in a catheter (e.g., a trans-catheter system), e.g., for aneurysmal disease treatment, or used as an endovascular graft.

Figure 6:
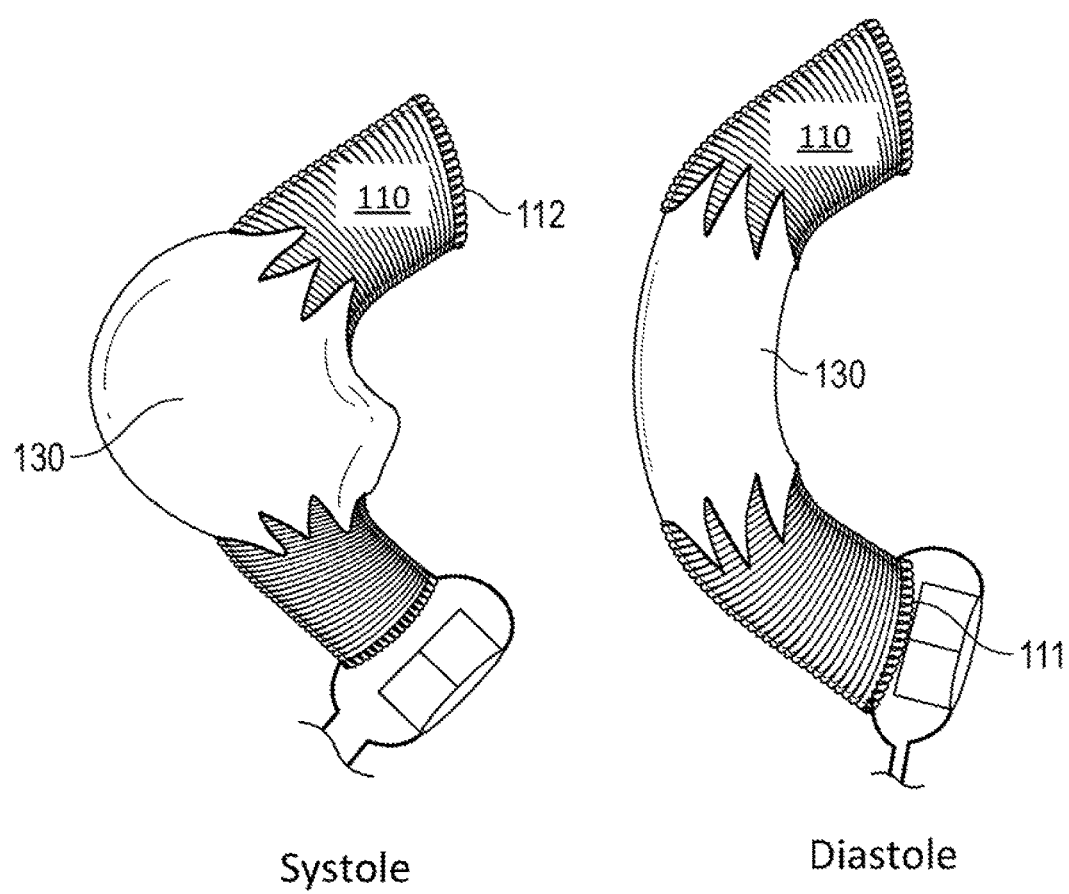
FIG. 6 shows the expansion of the expansible portion of the graft conduit during systole and the subsequent retraction of the expansible portion of the graft conduit during diastole.
Figure 7:
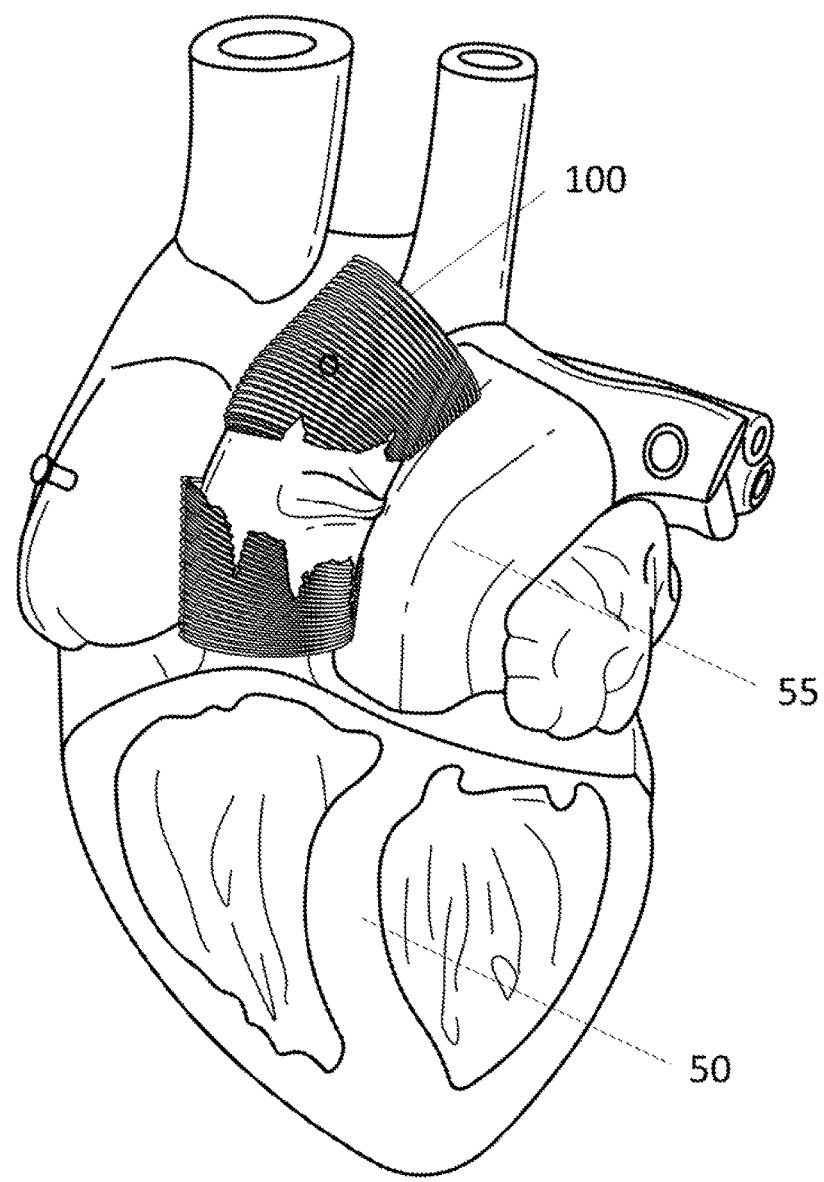
FIG. 7 shows a model heart (50) with a model aorta graft (55). Shown next to the model aorta graft (55) for comparison is an expansible cardiovascular graft system (100) which can be used as a graft for the ascending aorta (e.g., as an alternative to the model aorta graft (55) shown). This figure is not drawn to scale, nor is the expansible graft system (100) shown in the figure positioned in any particular limiting position.

The expansible cardiovascular graft system (100) of the present invention allows for gradual expansion (e.g., in systole) and recoil (e.g., in diastole) so as to absorb at least a portion of the left ventricular stroke volume in systole (see FIG. 6). Without wishing to limit the present invention to any theory or mechanism, it is believed that abrupt expansion of a graft system may cause problems such as (but not limited to) turbulence. Without wishing to limit the present invention to any theory or mechanism, it is believed that the system (100) of the present invention is advantageous because it may allow for more natural blood flow and may reduce stress on the heart.

In some embodiments, the system (100) of the present invention is adapted to accept between about 1 to 25% of the left ventricular stroke volume in systole. In some embodiments, the system (100) of the present invention is adapted to accept between about 1 to 50% of the left ventricular stroke volume in systole. In some embodiments, the system (100) of the present invention is adapted to accept between about 5 to 25% of the left ventricular stroke volume in systole. In some embodiments, the system (100) of the present invention is adapted to accept between about 5 to 50% of the left ventricular stroke volume in systole. In some embodiments, the system (100) of the present invention is adapted to accept between about 10 to 25% of the left ventricular stroke volume in systole. In some embodiments, the system (100) of the present invention is adapted to accept between about 10 to 50% of the left ventricular stroke volume in systole. In some embodiments, the system (100) of the present invention is adapted to accept between about 15 to 25% of the left ventricular stroke volume in systole. In some embodiments, the system (100) of the present invention is adapted to accept between about 15 to 50% of the left ventricular stroke volume in systole. In some embodiments, the system (100) of the present invention is adapted to accept between about 20 to 25% of the left ventricular stroke volume in systole. In some embodiments, the system (100) of the present invention is adapted to accept between about 20 to 50% of the left ventricular stroke volume in systole.

For example, in some embodiments, the system (100) of the present invention is adapted to accept about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, greater than 50%, etc., of the left ventricular stroke volume in systole. In some embodiments, the system (100) of the present invention is adapted to accept at least 1% of the left ventricular stroke volume in systole. In some embodiments, the system (100) of the present invention is adapted to accept at least 5% of the left ventricular stroke volume in systole. In some embodiments, the system (100) of the present invention is adapted to accept at least 10% of the left ventricular stroke volume in systole. In some embodiments, the system (100) of the present invention is adapted to accept at least 15% of the left ventricular stroke volume in systole. In some embodiments, the system (100) of the present invention is adapted to accept at least 20% of the left ventricular stroke volume in systole. In some embodiments, the system (100) of the present invention is adapted to accept at least 25% of the left ventricular stroke volume in systole. In some embodiments, the system (100) of the present invention is adapted to accept at least 30% of the left ventricular stroke volume in systole.

In some embodiments, the system (100) of the present invention is adapted to accept between about 1 to 5 cc of ventricular stroke volume. In some embodiments, the system (100) of the present invention is adapted to accept between about 5 to 15 cc of ventricular stroke volume. In some embodiments, the system (100) of the present invention is adapted to accept between about 5 to 20 cc of ventricular stroke volume. In some embodiments, the system (100) of the present invention is adapted to accept between about 10 to 15 cc of ventricular stroke volume. In some embodiments, the system (100) of the present invention is adapted to accept between about 10 to 20 cc of ventricular stroke volume. In some embodiments, the system (100) of the present invention is adapted to accept between about 10 to 25 cc of ventricular stroke volume. In some embodiments, the system (100) of the present invention is adapted to accept between about 15 to 20 cc of ventricular stroke volume. In some embodiments, the system (100) of the present invention is adapted to accept between about 15 to 25 cc of ventricular stroke volume. In some embodiments, the system (100) of the present invention is adapted to accept between about 15 to 30 cc of ventricular stroke volume. In some embodiments, the system (100) of the present invention is adapted to accept between about 20 to 25 cc of ventricular stroke volume. In some embodiments, the system (100) of the present invention is adapted to accept between about 20 to 30 cc of ventricular stroke volume. In some embodiments, the system (100) of the present invention is adapted to accept between about 15 to 35 cc of ventricular stroke volume. In some embodiments, the system (100) of the present invention is adapted to accept between about 20 to 35 cc of ventricular stroke volume. In some embodiments, the system (100) of the present invention is adapted to accept between about 10 to 35 cc of ventricular stroke volume. In some embodiments, the system (100) of the present invention is adapted to accept between about 5 to 40 cc of ventricular stroke volume. In some embodiments, the system (100) of the present invention is adapted to accept between about 10 to 40 cc of ventricular stroke volume. In some embodiments, the system (100) of the present invention is adapted to accept more than about 15 cc, more than about 20 cc, more than about 25 cc, more than about 30 cc, more than about 35 cc, more than about 40 cc, etc., of ventricular stroke volume. In some embodiments, the system (100) of the present invention is adapted to accept at least 5 cc of ventricular stroke volume. In some embodiments, the system (100) of the present invention is adapted to accept at least 10 cc of ventricular stroke volume. In some embodiments, the system (100) of the present invention is adapted to accept at least 15 cc of ventricular stroke volume. In some embodiments, the system (100) of the present invention is adapted to accept at least 20 cc of ventricular stroke volume. In some embodiments, the system (100) of the present invention is adapted to accept at least 25 cc of ventricular stroke volume. In some embodiments, the system (100) of the present invention is adapted to accept at least 30 cc of ventricular stroke volume.

Figure 2:
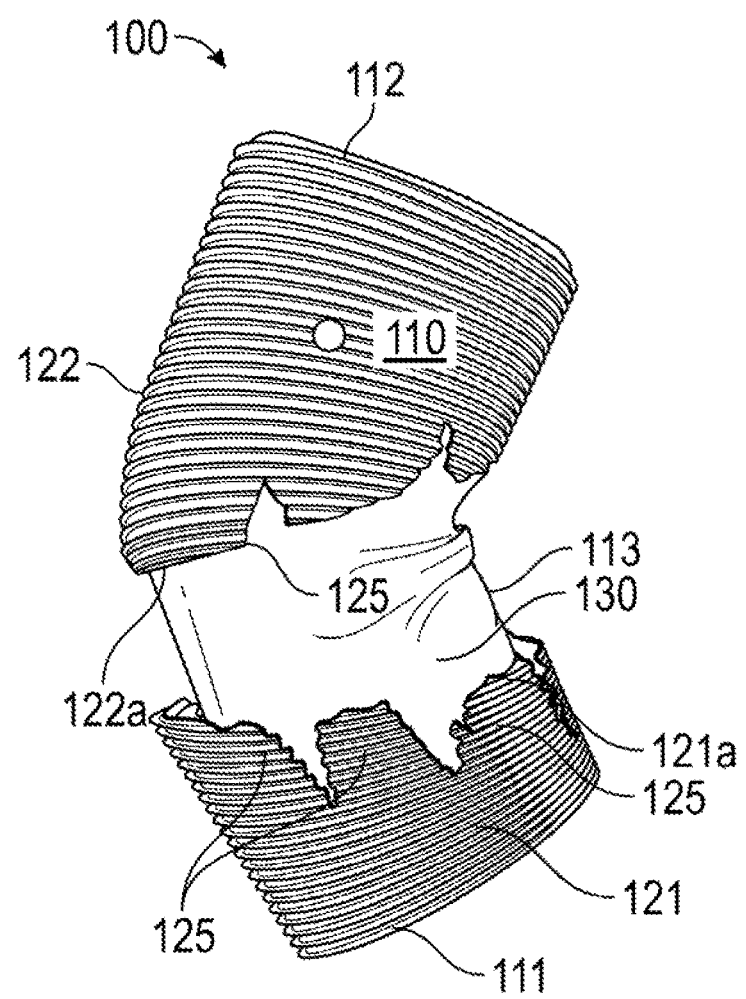
FIG. 2 shows a perspective view of the expansible cardiovascular graft system of the present invention.

As shown in FIG. 2, the system of the present invention comprises a graft conduit (110) having a proximal end (111), a distal end (112), and a midsection (113) between the proximal end (111) and distal end (112). Disposed at the proximal end (111) of the graft conduit (110) is a proximal anchor (121). Disposed at the distal end (112) of the graft conduit (110) is a distal anchor (122). The proximal anchor (121) and distal anchor (122) are separated by an expansible portion (130).

The expansible portion (130) is adapted to gradually expand in systole and recoil in diastole, allowing for absorption of a particular percentage of left ventricular stroke volume as previously described. In some embodiments, the anchors (121, 122) or a portion thereof may be rigid; in some embodiments, the anchors (121, 122) or a portion thereof may be slightly expansible. Generally, the anchors (121, 122) are not as expansible as is the expansible portion (130) of the graft conduit (110).

The anchors are the ends of the graft conduit (110) that are attached to the native vessel (e.g., aorta) or other appropriate tissue or secondary graft. Without wishing to limit the present invention to any theory or mechanism, it is believed that having the anchors (121, 122) or portions thereof (e.g., the portions at the proximal end 111 and distal end 112 of the graft conduit (110)) be rigid or only minimally expansible is advantageous because it allows for a more secure attachment to the native vessel (or other attachment site). Expansibility of the portions of the anchors (121, 122) at the proximal end 111 and distal end 112 of the graft conduit (110) may cause stress at the attachment sites, which may lead to graft failure. However, the present invention is not limited to configurations with rigid or only minimally expansible anchors (121, 122) (e.g., the portions at the proximal end 111 and distal end 112 of the graft conduit (110)).

In some embodiments, the inner edge (121a) of the proximal anchor (121) comprises serrations (125). In some embodiments, the inner edge (122a) of the distal anchor (122) comprises serrations (125). The serrations (125) may allow for a slight expansion of the area around the inner edges (121a, 122a) of the anchors (121, 122), which may help provide a gradual expansion of the expansible portion (130) of the graft conduit (110).

The graft conduit (110) shown in FIG. 2 shows a material used to create the expansible portion (130) extending the length of the graft conduit (110), e.g., from the proximal end (111) to the distal end (112), and the anchors (121) surround (or encase, or coat) the material at the proximal end (111) and distal end (112) of the graft conduit (110). The present invention is not limited to the configuration shown in FIG. 1. For example, in some embodiments, the expansible portion (130) extends to the inner edges (121a, 122a) of the anchors (121, 122) (e.g., to the serrations (125)). In some embodiments, the expansible portion (130) extends a distance past the inner edges (121a, 122a) of the anchors (121, 122) toward the proximal end (111) and distal end (112) of the graft conduit (110).

Figure 3A:
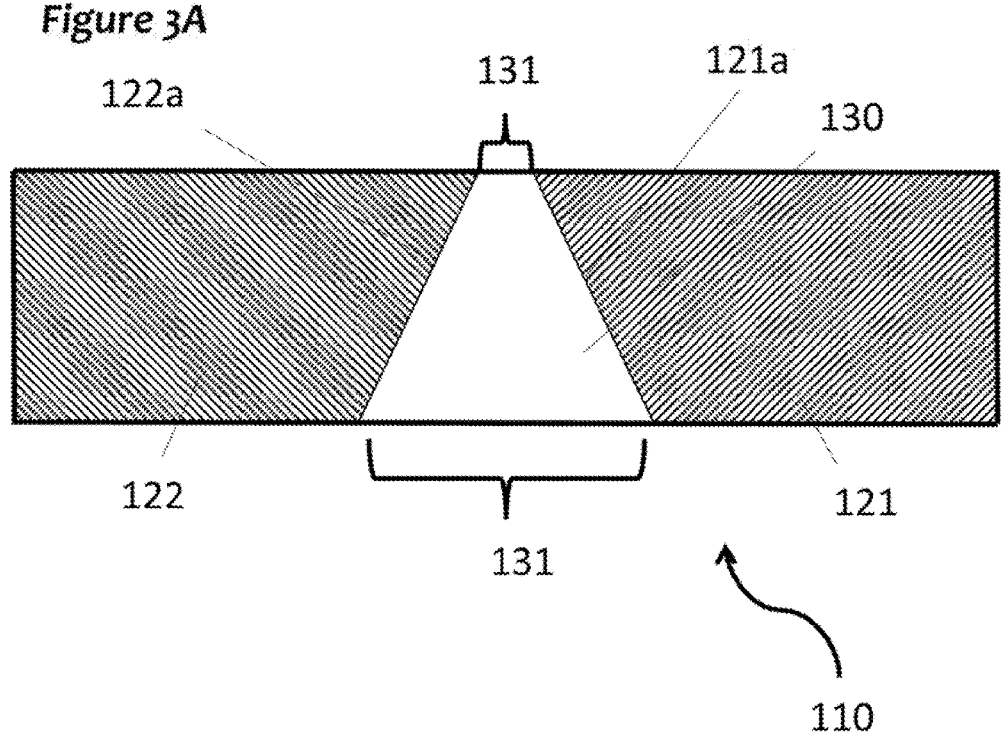
FIG. 3A and FIG. 3B show non-limiting examples of differently shaped expansible portions and anchors (not to scale). The inner edges of the anchors may or may not comprise serrations. Serrations are not shown in FIG. 3A and FIG. 3B. The present invention is not limited to linear graft conduits; in some embodiments, the graft conduit is curved (e.g., see FIG. 2).
Figure 3B:
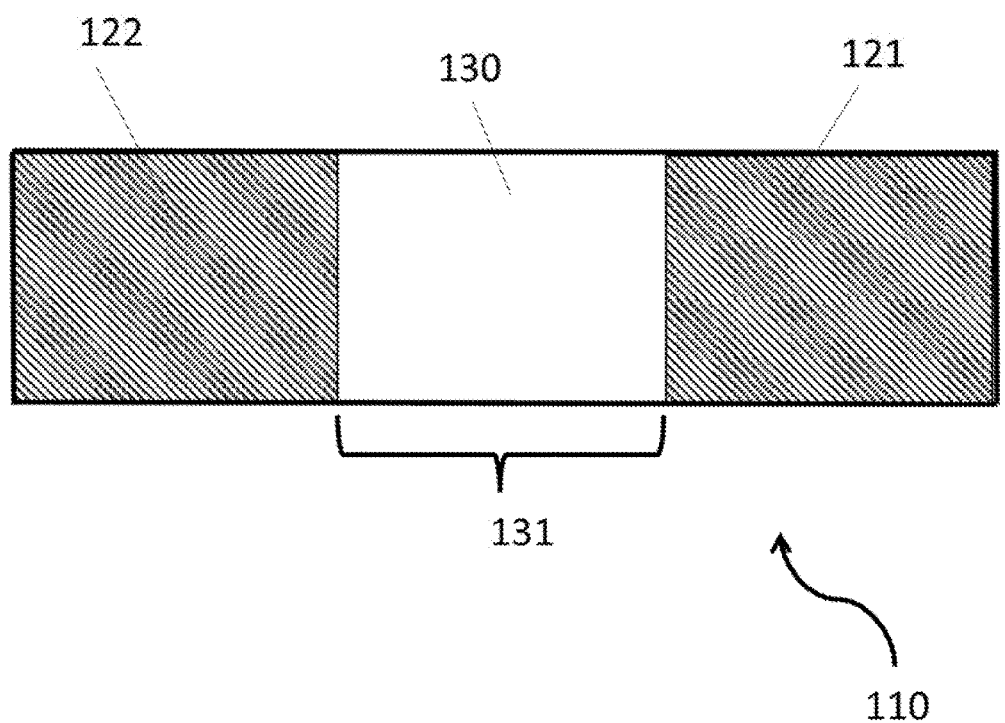

The example shown in FIG. 2 comprises a proximal anchor (121) and distal anchor (122) constructed from a polyethylene terephthalate (e.g., PET, PETE, PETP, Dacron®) vascular graft. This (or other similar material) may allow for good suturing to the attachment points of interest. An expansible tube (e.g., an elastic biocompatible polymer) lines the inner surface of the anchors (121, 122) and separates the anchors (121, 122) a first distance (131) (the first distance referring to the distance between the inner edge (121a) of the proximal anchor (121) to the inner edge (122a) of the distal anchor (122). In some embodiments, the first distance (131) is not uniform across the circumference of the expansible portion (130), e.g., one side of the expansible portion (130) may have a first distance (131) that is less than or greater to that of another side of the expansible portion (130). It can be seen in FIG. 3A that one side of the expansible portion (130) has a smaller first distance (131) than does the opposite side of the expansible portion (130). FIG. 3B shows an example wherein the expansible portion (130) has a uniform first distance (131) across its circumference. The differing first distances (131) may be a result of an anchor that has an inner edge at a particular angle (see FIG. 3A).

Figure 4:
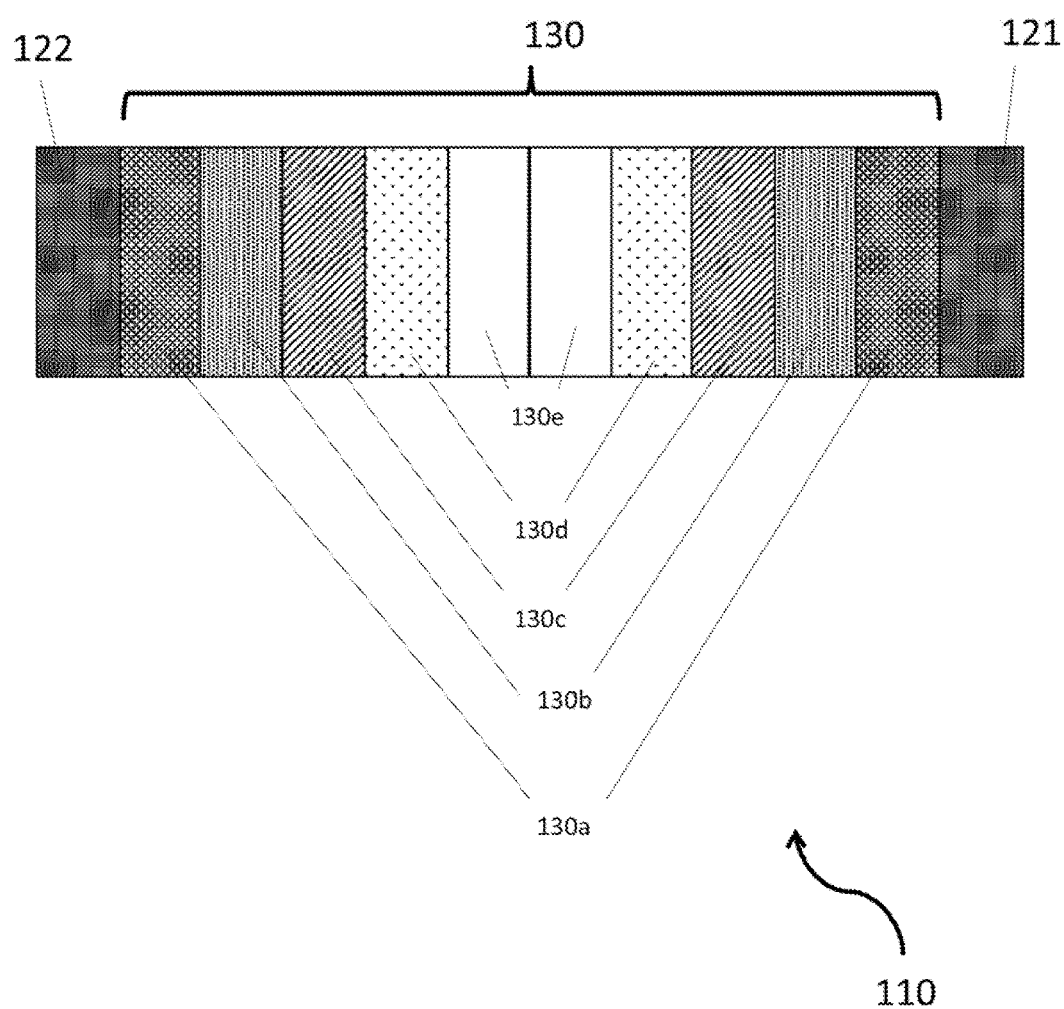
FIG. 4 shows an example of a graft conduit constructed from a gradient of expansible segments (not to scale).

The system (100) of the present invention, e.g., the graft conduit (110), is not limited to the particular construction shown in FIG. 2. For example, in some embodiments, the graft conduit (110) is constructed as a tube with a gradient of elasticity, e.g., the proximal end (111) and distal end (112) are least expansible and the midsection (113) or a portion thereof is the most expansible. FIG. 4 shows a non-limiting example of a graft conduit (110) constructed from a gradient of segments (e.g., expansible portion segments), wherein the expansible portion segments (e.g., first expansible portion segments (130a)) that are adjacent to the anchors (121, 122) are the least expansible relative to the other expansible portion segments, e.g., the second expansible portion segment (130b), the third expansible portion segment (130c), the fourth expansible portion segment (130d), the fifth expansible portion segment (130e), etc. Relative to the other expansible portion segments, the innermost expansible portion segments (e.g., the fifth expansible portion segments (130e)) may be the most expansible. The present invention is not limited to the configuration shown in FIG. 4. For example, the graft conduit may comprise more or less expansible segments, the shapes of the expansible portion segments (or anchors) may vary, etc. In some embodiments, the various segments (all or a portion thereof) of the gradient have differing thicknesses. In some embodiments, the various segments (all or a portion thereof) of the gradient comprise different materials.

Any appropriate configuration may be contemplated for the graft conduit (110) wherein at least a portion of the midsection (113) (e.g., the expansible portion (130)) is appropriately expansible (e.g., such that a portion of the graft conduit gradually expands appropriately during systole). The present invention is not limited to the configurations disclosed herein.

In some embodiments, the expansible portion (130) or a portion thereof is constructed from a material having a particular Young's modulus (elastic modulus) that is lower than that of the anchors (121, 122). The system (100) of the present invention is not limited to configuring the expansible portion (130) based on its Young's modulus. Any appropriate parameter may be considered, e.g., compliance, elastic limit, tensile strength, shear modulus, bulk modulus, etc.

In some embodiments, the system (100), e.g., the graft conduit (110) is coated. For example, in some embodiments, all or a portion of the outer surface of the graft conduit (110) comprises a coating. Without wishing to limit the present invention to any theory or mechanism, it is believed that it is possible that over time the graft may become encased in scar tissue, which may limit the expansibility of the graft. In some embodiments, a coating may help reduce scar tissue deposits on the graft conduit (110). In some embodiments, a coating may slow down the deposition of scar tissue on the graft conduit (110). In some embodiments, a coating does not affect the deposition of scar tissue on the graft conduit (110). In some embodiments, the use of the graft conduit (110) with a catheter (140) may help reduce scar tissue build up on the graft conduit (110) and subsequent limiting of the expansibility of the graft (110).

In some embodiments, all or a portion of the inner surface of the graft conduit (110) comprises a coating. In some embodiments, the coating may block or inhibit any plaque formation (or other materials that may build up on the inner surface of the graft conduit (110) inside the graft conduit (110). In some embodiments, the coating does not have any effect on plaque formation (or other materials that may build up on the inner surface of the graft conduit (110)) inside the graft conduit (110).

The system (100) of the present invention may be constructed in a variety of sizes (e.g., lengths). For example, the graft conduit (110) may be constructed to be long enough distally to accept a coronary bypass graft proximal anastomosis. In some embodiments, the ends (111, 112) of the graft conduit (110) can be trimmed, e.g., by the surgeon, to fit variations in size and geometry of the native aorta or other attachment site.

In some embodiments, the anchors (121, 122) are at least 1 mm in length (e.g., from the respective end (111, 112) of the graft conduit (110) to the respective inner edge (121a, 122a) of the anchor (121, 122)). In some embodiments, the anchors (121, 122) are at least 2 mm in length (e.g., from the respective end (111, 112) of the graft conduit (110) to the respective inner edge (121a, 122a) of the anchor (121, 122)). In some embodiments, the anchors (121, 122) are at least 3 mm in length (e.g., from the respective end (111, 112) of the graft conduit (110) to the respective inner edge (121a, 122a) of the anchor (121, 122)). In some embodiments, the anchors (121, 122) are at least 4 mm in length (e.g., from the respective end (111, 112) of the graft conduit (110) to the respective inner edge (121a, 122a) of the anchor (121, 122)). In some embodiments, the anchors (121, 122) are at least 5 mm in length (e.g., from the respective end (111, 112) of the graft conduit (110) to the respective inner edge (121a, 122a) of the anchor (121, 122)). In some embodiments, the anchors (121, 122) are at least 6 mm in length (e.g., from the respective end (111, 112) of the graft conduit (110) to the respective inner edge (121a, 122a) of the anchor (121, 122)). In some embodiments, the anchors (121, 122) are at least 7 mm in length (e.g., from the respective end (111, 112) of the graft conduit (110) to the respective inner edge (121a, 122a) of the anchor (121, 122)). In some embodiments, the anchors (121, 122) are at least 8 mm in length (e.g., from the respective end (111, 112) of the graft conduit (110) to the respective inner edge (121a, 122a) of the anchor (121, 122)). In some embodiments, the anchors (121, 122) are at least 9 mm in length (e.g., from the respective end (111, 112) of the graft conduit (110) to the respective inner edge (121a, 122a) of the anchor (121, 122)). In some embodiments, the anchors (121, 122) are at least 1 cm in length (e.g., from the respective end (111, 112) of the graft conduit (110) to the respective inner edge (121a, 122a) of the anchor (121, 122)). In some embodiments, the anchors (121, 122) are at least 1.25 cm in length (e.g., from the respective end (111, 112) of the graft conduit (110) to the respective inner edge (121a, 122a) of the anchor (121, 122)). In some embodiments, the anchors (121, 122) are at least 1.5 cm in length (e.g., from the respective end (111, 112) of the graft conduit (110) to the respective inner edge (121a, 122a) of the anchor (121, 122). In some embodiments, the anchors (121, 122) are at least 1.75 cm in length (e.g., from the respective end (111, 112) of the graft conduit (110) to the respective inner edge (121a, 122a) of the anchor (121, 122). In some embodiments, the anchors (121, 122) are at least 2 cm in length (e.g., from the respective end (111, 112) of the graft conduit (110) to the respective inner edge (121a, 122a) of the anchor (121, 122). In some embodiments, the anchors (121, 122) are at least 2.5 cm in length (e.g., from the respective end (111, 112) of the graft conduit (110) to the respective inner edge (121a, 122a) of the anchor (121, 122). In some embodiments, the anchors (121, 122) are at least 3 cm in length (e.g., from the respective end (111, 112) of the graft conduit (110) to the respective inner edge (121a, 122a) of the anchor (121, 122). In some embodiments, the anchors (121, 122) are at least 4 cm in length (e.g., from the respective end (111, 112) of the graft conduit (110) to the respective inner edge (121a, 122a) of the anchor (121, 122). In some embodiments, the anchors (121, 122) are at least 5 cm in length (e.g., from the respective end (111, 112) of the graft conduit (110) to the respective inner edge (121a, 122a) of the anchor (121, 122).

In some embodiments, the graft conduit (110) (or a portion thereof) is curved. In some embodiments, the graft conduit (110) (or a portion thereof) is linear.

Figure 5A:
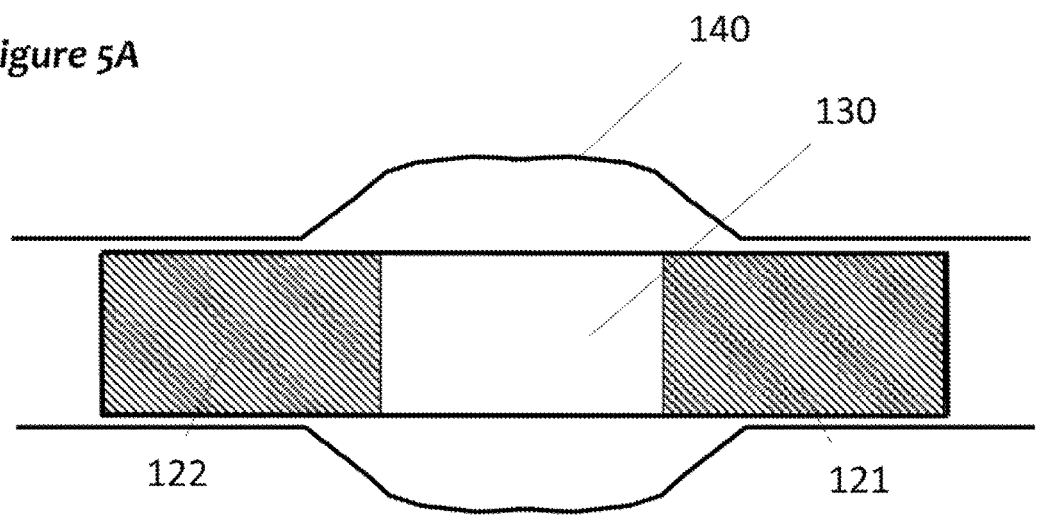
FIG. 5A and FIG. 5B show non-limiting examples of a graft conduit encased in a catheter (not to scale).
Figure 5B:
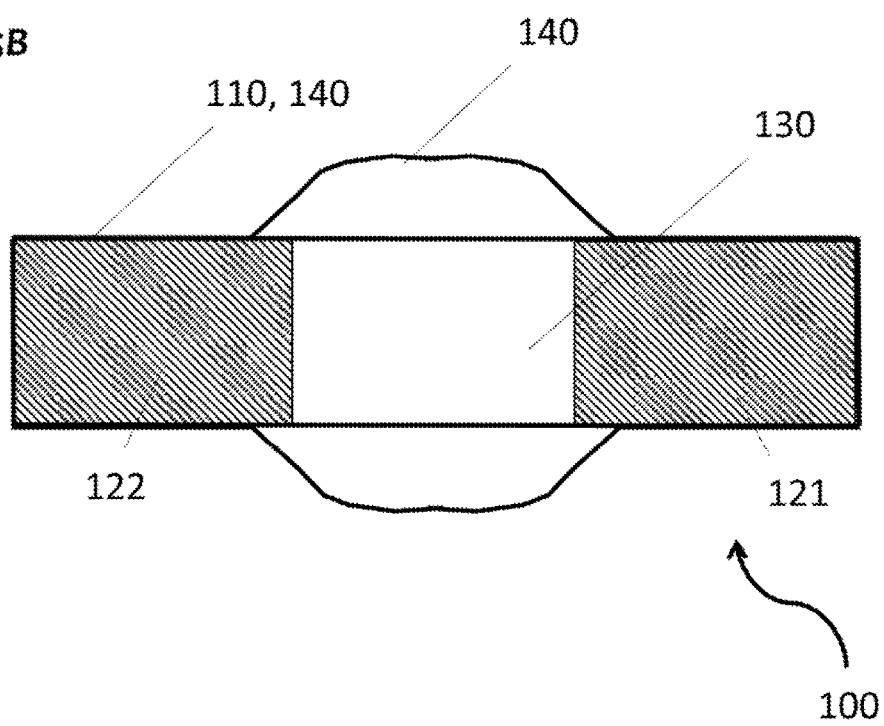

In some embodiments, the graft conduit (110) or a portion thereof is coated. In some embodiments, the graft conduit (110) or a portion thereof is encased in a secondary tube or conduit. In some embodiments, the system (100) comprises a catheter (140) that at least partially encases or covers the graft conduit (110). FIG. 5A and FIG. 5B show non-limiting examples of graft conduits (110) encased in a catheter (140). In some embodiments, the portion of the catheter (140) that covers the expansible portion (130) of the graft conduit (110) is larger in diameter as compared to the portion of the catheter (140) that covers at least a part of the anchors (121, 122). In some embodiments, the diameter of the catheter (140) is generally uniform but at least large enough to allow for the expansible portion (130) of the graft conduit (110) to expand appropriately. In some embodiments, at least a portion of the graft conduit (110) is integrated in the catheter (140) (see FIG. 5B).

Figure 8A:
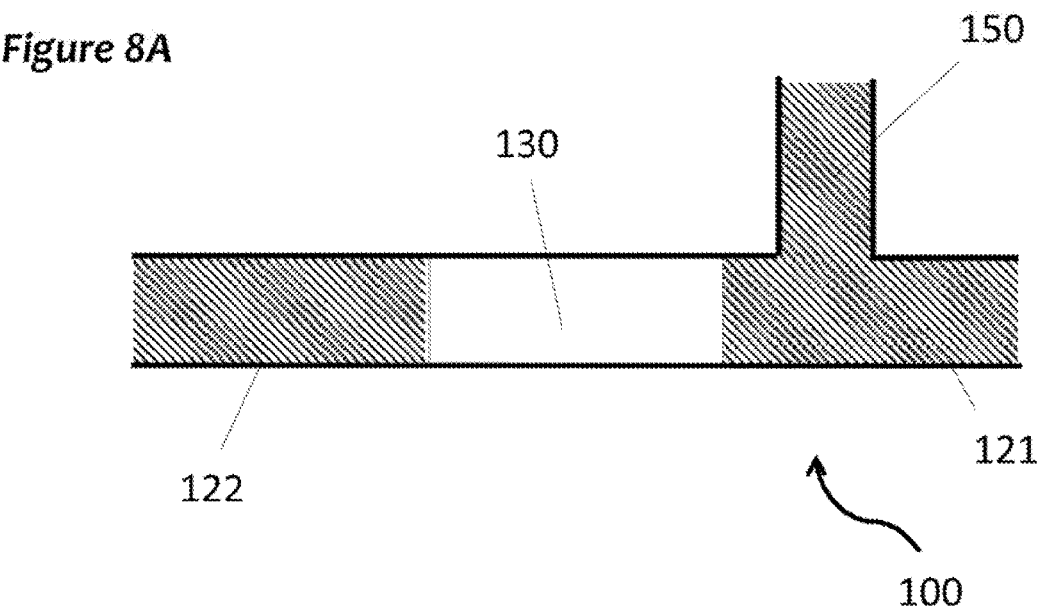
FIG. 8A and FIG. 8B show non-limiting examples of graft conduits comprising secondary channels for grafting of a secondary artery in addition to the aorta. The graft conduit is not limited to a linear configuration. In some embodiments, the graft conduit is curved. The secondary channel may or may not comprise its own expansible portion.
Figure 8B:
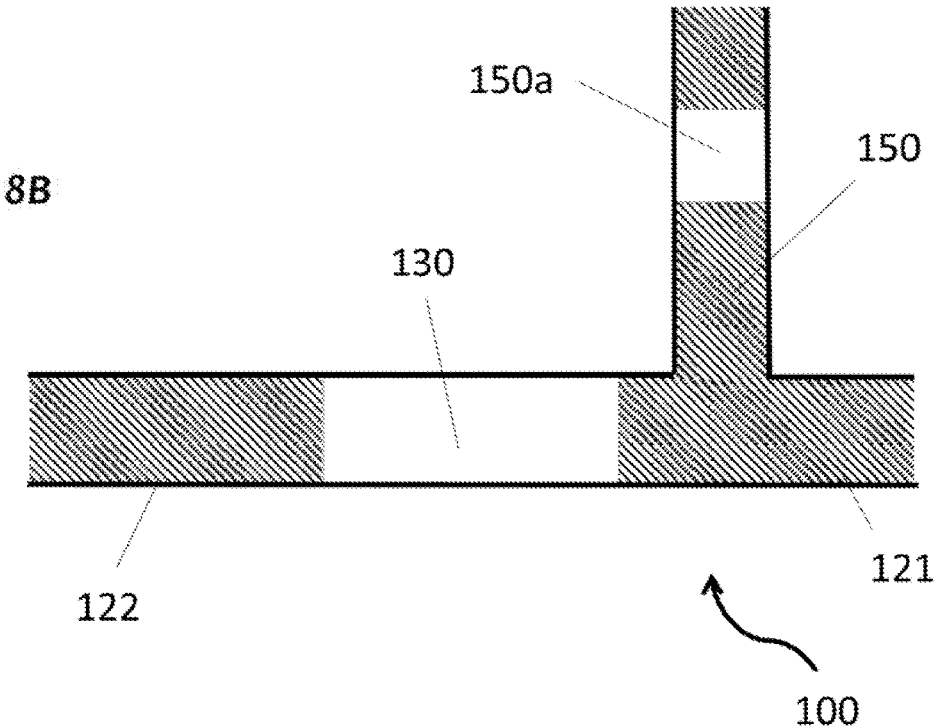
Figure 9:
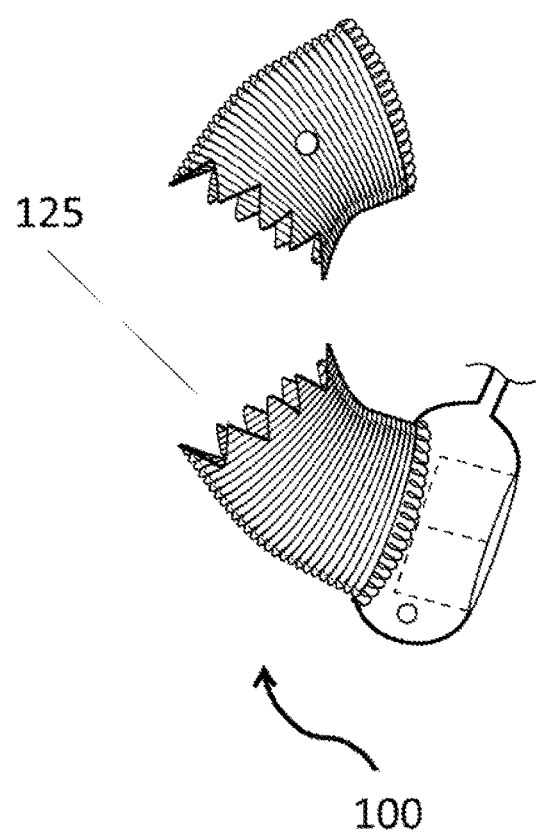
FIG. 9 shows that if a coronary bypass graft proximal anastomosis is needed, it may be made to the distal aspect, through the double layer of vascular graft and interior lining. Note the serrations (125) for gradual expansion.

As shown in FIG. 8, in some embodiments, the system (100) of the present invention comprises one or more additional channels. For example, a secondary channel (150) (or more than one secondary channels) is fluidly connected to a portion of the graft conduit (110), e.g., a portion of an anchor (121, 122) and/or a portion of the expansible portion (130). The secondary channel may allow for grafting of additional arteries (e.g., in addition to the aorta) such as but not limited to the brachiocephalic artery, the left common carotid artery, the left subclavian artery, etc. In some embodiments, the secondary channel (150) comprises an expansible portion (150a).

METHODS OF USE

The present invention also features methods of treating cardiovascular conditions through the use of expansible cardiovascular graft systems (100) of the present invention. Cardiovascular conditions that may be treated with the expansible cardiovascular graft system (100) of the present invention may include but is not limited to aneurysmal disease and decreased arterial compliance. In some embodiments, the vessel grafting may be subsequent to aortic valve replacement (AVR). As previously discussed, the expansible cardiovascular graft system (100) allows for gradual expansion (e.g., in systole) and recoil (e.g., in diastole).

In some embodiments, the method comprises replacing a portion of the aorta with the expansible cardiovascular graft system (100) of the present invention. In some embodiments, the portion of the aorta includes but is not limited to the ascending aorta or the descending aorta. The present invention is not limited to use in the aorta.

In some embodiments, the attachment site of the system (100) is at or near the sinotubular junction and the distal ascending aorta, e.g., the proximal end (111) of the graft conduit (110) is attached at the sinotubular junction and the distal end (112) of the graft conduit (110) is attached to the distal ascending aorta. In some embodiments, the system (100) of the present invention replaces all or a portion of the aortic arch. In some embodiments, the system (100) of the present invention replaces all or a portion of the ascending aorta. In some embodiments, the system (100) of the present invention replaces a portion of the descending aorta (e.g., infrarenal aorta). In some embodiments, the system (100) of the present invention replaces all or a portion of the aortic root.

In some embodiments, the method comprises utilizing a system comprising a catheter. In some embodiments, the method comprises utilizing the system of the present invention for an endovascular graft.

EXAMPLES

The following section describes non-limiting examples of graft systems (100) and methods of use.

Ascending aorta: The system may be used for replacement of ascending aorta at the time of aortic valve replacement or another form of heart operation. The outer layer of the device may be a standard vascular graft, and may be sewn to the sino-tubular junction, and may be sewn to the aorta near the innominate artery distally. If a coronary bypass graft proximal anastomosis is needed, it may be made to the distal aspect, through the double layer of vascular graft and interior lining (see FIG. 9).

Descending thoracic aorta: If done as open operation, a straight or gently curved graft may be sewn as usual to the proximal descending aorta near the arch, and distally toward the diaphragm. If done as a trans-catheter endovascular graft, then it may be done as is usually practiced with proximal anchoring near the arch, and distal anchoring in a suitable segment. Multiple grafts may be deployed to get proper distal seating and length; the relatively non-expansible stable neck portions of the grafts may overlap for secure fit, with midsections free to expand and recoil.

Infra-renal aorta: If open, it may be sewn as usual to the aorta just below the renal arteries and to the aorta before the iliac bifurcation. If the iliac vessels need replacement, the graft may bifurcate into two limbs: these limbs may or may not have expansible capability with taper to sewing area. If done as endovascular graft, the same principles may apply: standard infra-renal non-expansible neck, expansible midsection, and possibly expansible iliac limbs.

The potential materials that may be used include but are not limited to medical segmented polyurethanes. Without wishing to limit the present invention to any theory or mechanism, materials such as medical segmented polyurethanes may possess a combination of properties that may be useful for the system of the present invention, e.g., the sustained high modulus of elasticity, physiological compatibility, resistance to flex-fatigue exhibited by segmented polyurethane, etc. (the resistance to flex-fatigue may be responsible for successful performance of the commercial Total Artificial Heart (TAH)). Properties of this material allow different thicknesses to achieve a range of compliances. Segmented polyurethane may be molded into complex shapes, and controlled to exacting specifications of density, dimensions and surface finish.

The disclosures of the following U.S. Patent and documents are incorporated in their entirety by reference herein: U.S. Pat. Nos. 8,728,152; 7,758,633; 7,318,838; 6,352,554; WO 2004/021925; U.S. Pat. Nos. 8,221,492; 7,717,952; 8,388,679; 7,655,035; 7,658,706; 7,722,665; 7,785,438; 7,806,922; 7,833,263; 7,857,843; 7,901,446; 8,038,690; 8,066,758; 8,123,797; 8,163,002; 8,353,814; 8,475,477; Bentall and DeBono (1968) Thorax 23(4):338-9; Vara et al. (2005) Pathol Biol (Paris) 53(10):599-612; De Paulis et al. (2008) Ann Thorac Surg 309, 85:305-9; Nishibe et al. (2007) Vascular 15(6):356-60; Kirsch et al. (2009) Eur J Cardiothorac Surg 35(1):77-82; Kouchoukos et al. (1980) Ann Surg 192(3):403-412; Kelley et al., 1989, Circulation 80:1652-1659; Scuteri, 2013, Intern Journ Cardiol 169:371-377; Merillon, 2014, Arch Cardiovas Disease 107:554-562; Benetos et al., 2002, Am Journ Hyperten 15:1101-1108; Asmar et al., 1995, Blood Pressure 4:48-54.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. An expansible cardiovascular graft system (100) comprising: a graft conduit (110) having a proximal end (111) and a distal end (112) and having corrugations (200) stacked from the proximal end (111) to the distal end (112), wherein a proximal anchor (121) is disposed at the proximal end (111) of the graft conduit (110) and an inner edge (121a) of the proximal anchor (121) comprises serrations (125) that cut across the stacked corrugations (200) of the graft conduit and a distal anchor (122) is disposed at the distal end (112) of the graft conduit (110) and an inner edge (122*a*) of the distal anchor (122) comprises serrations (125) that cut across the stacked corrugations (200) of the graft conduit; and an expansible portion (130) is disposed between the proximal anchor (121) and the distal anchor (122), wherein the serrations allow the expansible portion (130) to gradually expand in systole and recoil in diastole.

2. The system (100) of claim 1, wherein the system (100) absorbs at least a portion of left ventricular stroke volume in systole.

3. The system (100) of claim 2, wherein the system (100) absorbs at least 5 cc of ventricular stroke volume.

4. The system (100) of claim 2, wherein the system (100) absorbs at least 15 cc of ventricular stroke volume.

5. The system (100) of claim 1, wherein the proximal end (111) and the distal end (112) of the graft conduit (110) are rigid or non-compliant.

6. The system (100) of claim 1, wherein the proximal anchor (121), the distal anchor (122), both the proximal anchor (121) and distal anchor (122), or a portion thereof are rigid or non-compliant.

7. The system (100) of claim 1, wherein a portion of the proximal anchor (121), the distal anchor (122), or both the proximal anchor (121) and distal anchor (122) is expansible.

8. The system (100) of claim 1, wherein material of the expansible portion (130) extends a length of the graft conduit (110).

9. The system (100) of claim 1, wherein the proximal anchor (121) and distal anchor (122) encase or coat at least a portion of the expansible portion (130).

10. The system (100) of claim 1, wherein the expansible portion comprises a plurality of expansible portion segments to form a gradient of elasticity.

11. The system (100) of claim 1, wherein the proximal anchor (121) and distal anchor (122) are constructed from a material that is less compliant than that of the expansible portion (130).

12. The system (100) of claim 1, wherein the graft conduit (110) or a portion thereof is coated.

13. The system (100) of claim 1, wherein the graft conduit (110) or a portion thereof is encased in a secondary tube or conduit.

14. The system (100) of claim 1 further comprising a catheter (140), wherein the graft conduit (110) is disposed inside the catheter (140).

15. The system (100) of claim 1 further comprising a catheter (140), wherein the graft conduit (110) is integrated into the catheter (140).

16. The system (100) of claim 1 further comprising a secondary channel (150) fluidly connected to the proximal anchor (121), the distal anchor (122), the expansible portion (130), a combination thereof, or a portion thereof.

17. The system (100) of claim 16, wherein the secondary channel (150) comprises an expansible portion (150*a*).

18. A method of replacing a portion of a vessel, said method comprising: a) providing an expansible cardiovascular graft system, said system comprises a graft conduit (110) having a proximal end (111) and a distal end (112) and having corrugations (200) stacked between the proximal end and the distal end, wherein a proximal anchor (121) is disposed at the proximal end (111) of the graft conduit (110) and an inner edge (121*a*) of the proximal anchor (121) comprises serrations that cut across the stacked corrugations (200) and wherein a distal anchor (122) is disposed at the distal end (112) of the graft conduit (110) and an inner edge (122*a*) of the distal anchor (122) comprises serrations (125) that cut across the stacked corrugations; and an expansible portion (130) is disposed between the proximal anchor (121) and the distal anchor (122), wherein the serrations allow the expansible portion (130) to gradually expand in systole and recoil in diastole; b) inserting into the vessel the expansible cardiovascular graft system (100); and c) suturing the proximal end (111) of the graft conduit (110) to a first attachment site of the vessel and suturing the distal end (112) of the graft conduit (110) to a second attachment site of the vessel.

19. The method of claim 18, wherein the vessel includes a portion of the aorta.

20. The method of claim 18, wherein the first attachment site is a sinotubular junction and the second attachment site is a distal ascending aorta.

* * * * *